(12) United States Patent
Unger et al.

(10) Patent No.: US 10,518,073 B2
(45) Date of Patent: Dec. 31, 2019

(54) DELIVERY SYSTEM AND PROCESS

(71) Applicant: SEAGULL IP PTY. LTD., Toorak, Victoria (AU)

(72) Inventors: Harry Unger, Melbourne (AU); Mark Unger, Melbourne (AU); Donald Martin, Killara (AU); David John Bull, Riverview (AU); Craig Andrews, Mosman (AU)

(73) Assignee: PolyPharma Pty Ltd, Toorak, Victoria (AU)

( * ) Notice: Subject to any disclaimer, the term of this patent is extended or adjusted under 35 U.S.C. 154(b) by 0 days.

(21) Appl. No.: 14/502,405

(22) Filed: Sep. 30, 2014

(65) Prior Publication Data

US 2015/0018752 A1 Jan. 15, 2015

Related U.S. Application Data

(63) Continuation of application No. 12/304,960, filed as application No. PCT/AU2007/000843 on Jun. 15, 2007, now abandoned.

(Continued)

(51) Int. Cl.
*A61M 37/00* (2006.01)
*A61F 9/00* (2006.01)
(Continued)

(52) U.S. Cl.
CPC ....... *A61M 37/0092* (2013.01); *A61F 9/0017* (2013.01); *A61K 9/0009* (2013.01);
(Continued)

(58) Field of Classification Search
CPC .......... A61F 9/0017; A61F 2009/00865; A61F 2009/0087; A61F 2009/00863;
(Continued)

(56) References Cited

U.S. PATENT DOCUMENTS 1,577,551 A  3/1926 Attendu
3,961,628 A * 6/1976 Arnold .................. A61F 9/0017
                                                         424/427

(Continued)

FOREIGN PATENT DOCUMENTS

EP        0182765 A2   5/1986
EP       0 278 074 A   8/1988
(Continued)

OTHER PUBLICATIONS

Notice of Reasons for Rejection in Japanese Application No. 2014-195934 dated Aug. 11, 2015 in 2 pages.

(Continued)

*Primary Examiner* — Brandy S Lee
(74) *Attorney, Agent, or Firm* — Knobbe, Martens, Olson & Bear LLP

(57) ABSTRACT

A delivery system, including: a material for storing molecules and/or nanoparticles by substantially binding said molecules and/or nanoparticles to said material; a means for applying an electric field to said material to release said molecules and/or nanoparticles; and a means for applying an ultrasonic signal to said material to transport said molecules and/or nanoparticles through said material to a surface for delivery to an entity.

36 Claims, 13 Drawing Sheets

Related U.S. Application Data

Figure 1:
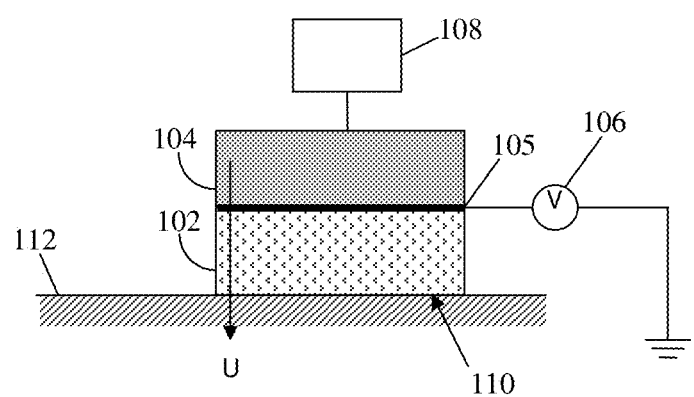

(60) Provisional application No. 60/814,093, filed on Jun. 15, 2006.

(51) Int. Cl.
*A61K 9/00* (2006.01)
*A61K 47/32* (2006.01)
*A61N 1/32* (2006.01)

(52) U.S. Cl.
CPC ......... *A61K 47/32* (2013.01); *A61M 37/0076* (2013.01); *A61N 1/327* (2013.01)

(58) Field of Classification Search
CPC . A61K 9/0009; A61K 47/32; A61M 37/0092; A61M 37/0076; A61M 2205/18; A61M 5/14276; A61M 5/16854; A61M 5/172; A61N 1/30; A61N 1/327; A61N 5/0622; A61N 1/36046; A61N 2005/0648; A61B 5/4839; A61B 2090/378; A61B 17/320068; A61B 2562/0238; A61B 5/1455; H01M 4/36
See application file for complete search history.

(56) References Cited

U.S. PATENT DOCUMENTS

| | | | |
|---|---|---|---|
| 4,057,619 A * | 11/1977 | Higuchi | A61K 9/0051 424/427 |
| 4,585,652 A | 4/1986 | Miller et al. | |
| 5,115,805 A | 5/1992 | Bommannan et al. | |
| 5,415,629 A | 5/1995 | Henley | |
| 5,445,611 A | 8/1995 | Eppstein et al. | |
| 5,618,275 A * | 4/1997 | Bock | A61B 17/20 601/2 |
| 5,658,247 A | 8/1997 | Henley | |
| 5,807,258 A | 9/1998 | Cimochowski et al. | |
| 5,882,677 A | 3/1999 | Kupperblatt | |
| 6,041,253 A | 3/2000 | Kost et al. | |
| 6,049,733 A * | 4/2000 | Phipps | A61N 1/0448 424/449 |
| 6,322,532 B1 | 11/2001 | D'Sa et al. | |
| 6,440,096 B1 | 8/2002 | Lastovich et al. | |
| 6,477,410 B1 * | 11/2002 | Henley | A61N 1/0428 601/1 |
| 6,706,032 B2 * | 3/2004 | Weaver | A61M 5/427 128/898 |
| 6,792,306 B2 * | 9/2004 | Henley | A61N 1/044 604/20 |
| 7,850,645 B2 | 12/2010 | Atanasoska et al. | |
| 8,870,810 B2 | 10/2014 | Mitragotri et al. | |
| 2002/0099356 A1 | 7/2002 | Unger et al. | |
| 2002/0115957 A1 | 8/2002 | Sun et al. | |
| 2002/0130837 A1 | 9/2002 | Johnston, Jr. et al. | |
| 2003/0167033 A1 * | 9/2003 | Chen | A61B 5/411 604/20 |
| 2004/0171980 A1 * | 9/2004 | Mitragotri | A61K 49/0004 604/20 |
| 2005/0048044 A1 * | 3/2005 | Schwartz | A61K 38/482 424/94.1 |
| 2005/0153873 A1 | 7/2005 | Chan et al. | |
| 2006/0184092 A1 | 8/2006 | Atanasoska et al. | |
| 2007/0004973 A1 * | 1/2007 | Tan | A61K 9/0009 600/309 |
| 2007/0031495 A1 | 2/2007 | Eppstein et al. | |
| 2007/0232983 A1 | 10/2007 | Smith | |
| 2009/0209899 A1 | 8/2009 | Unger et al. | |
| 2009/0326441 A1 | 12/2009 | Iliescu et al. | |

FOREIGN PATENT DOCUMENTS

| | | | |
|---|---|---|---|
| EP | 0 337 642 A2 | 10/1989 | |
| EP | 1 563 851 A1 | 8/2005 | |
| JP | S52-64335 A | 5/1977 | |
| JP | S52-115591 A | 9/1977 | |
| JP | 61-196967 | 9/1986 | |
| JP | S63-135179 A | 6/1988 | |
| JP | 03170172 | 7/1992 | |
| JP | 11-155962 | 6/1999 | |
| JP | 2003-512318 A | 4/2003 | |
| JP | 2003-534108 T2 | 11/2003 | |
| JP | 2005-522283 A | 7/2005 | |
| JP | 2006-516215 A | 6/2006 | |
| WO | WO 98/00194 A1 | 1/1998 | |
| WO | WO99/66980 * | 6/1999 | ............ A61M 37/00 |
| WO | WO 99/66980 A1 | 12/1999 | |
| WO | WO 01/28529 A1 | 4/2001 | |
| WO | WO 01/91853 A1 | 10/2001 | |
| WO | WO 02/056939 A2 | 7/2002 | |
| WO | WO 2004/105864 A1 | 12/2004 | |
| WO | WO 2004/113422 A2 | 12/2004 | |
| WO | WO 2005/077422 A1 | 8/2005 | |
| WO | WO 2007/081750 A2 | 7/2007 | |

OTHER PUBLICATIONS

Final Rejection in Japanese Application No. 2014-008183 dated Sep. 24, 2015 in 2 pages.
Definition of iontophoresis obtained from www.dictionary.com, retrieved Aug. 11, 2010.
Definition of iontophoresis obtained from www.mercksource.com, retrieved Aug. 11, 2010.
Examination Report in Australian Application No. 2015203712, dated May 19, 2016.
Supplementary European Search Report in corresponding European Application No. EP 07 71 9085, dated Jul. 31, 2013.

* cited by examiner

DELIVERY SYSTEM AND PROCESS

FIELD

The present invention relates to a delivery system and process, and in particular to a process and device for delivering nanoparticles and/or molecules such as drugs, peptides, and/or hormones to biological tissues, or inks or dyes to a variety of materials, including paper and skin.

BACKGROUND

The delivery and incorporation of molecules such as drugs, hormones, peptides or dyes into inert or biological materials can be achieved by a number of mechanisms. For inert materials, cost and quality of delivery is required. In biological systems, such as animals and humans, issues of safety of delivery are also important. Delivery of drugs into animals or humans can occur either orally, by injection at the site, or systemically. Many drugs require injection to achieve the desired therapeutic outcome. However, for some conditions and diseases, the risks associated with injection can outweigh the benefits. Injection also requires a higher level of skill. Injection in areas of greater sensitivity and risk, also often require sterile conditions and more involved patient care. For example, to deliver a steroid drug to the back of the eye for treatment of age-related macular degeneration requires injection into the eye with a high risk of intraocular infection and retinal detachment, the most common side-effects associated with injecting therapeutic agents directly into the eye.

It is desired to provide a delivery process and system and a delivery component for the system that alleviate one or more of the above difficulties, or at least provide a useful alternative.

SUMMARY

In accordance with the present invention, there is provided a delivery process, including:
  applying an electric field to a material to release molecules and/or particles substantially bound within said material; and
  applying an ultrasonic signal to said material to transport said molecules and/or particles through said material to a surface for delivery to an entity placed in contact with said surface.

Preferably, said material includes a polymeric material or a ceramic material.

Preferably, said polymeric material includes at least one of an electro-conductive polymer and a cross-linked polymeric gel.

Advantageously, said cross-linked polymeric gel may be a hydrogel.

Advantageously, said molecules may include one or more drugs for delivery to biological tissues.

Advantageously, said molecules may be contained within particles substantially bound within said material.

Advantageously, said particles may include nanoparticles.

Preferably, said biological tissues include mucosal tissues.

Advantageously, said biological tissues may include an eye or ocular adnexae, buccal or gingival mucosa and teeth, anal or vaginal mucosa, or skin.

Advantageously, said nanoparticles may incorporate one or more drugs, hormones, and/or peptides or other molecules for delivery to biological tissues.

Advantageously, said molecules may include an ink or dye for printing or marking said external entity.

Advantageously, the process may include controlling an intensity of said ultrasonic signal to determine a depth of said printing or marking in said entity.

Advantageously, said entity may include skin.

Advantageously, the process may include applying said molecules or nanoparticles to said material to substantially bind said molecules or nanoparticles within said material prior to the application of said electric field.

The present invention also provides a system having components for executing the steps of any one of the above processes.

The present invention also provides a device having components for executing the steps of any one of the above processes.

In accordance with the present invention, there is also provided a delivery system, including:
  a material for storing molecules and/or nanoparticles by substantially binding said molecules and/or nanoparticles to said material;
  means for applying an electric field to said material to release said molecules and/or nanoparticles; and
  means for applying an ultrasonic signal to said material to transport said molecules and/or nanoparticles through said material to a surface for delivery to an entity.

Preferably, said material includes a polymeric material or a ceramic material.

Preferably, said polymeric material includes at least one of an electro-conductive polymer and a cross-linked polymeric gel.

Advantageously, said cross-linked polymeric gel may include a hydrogel.

Preferably, said means for applying an ultrasonic signal includes at least one ultrasonic transducer attached to said polymeric material or a ceramic material.

Advantageously, said polymeric material may include an electro-conductive polymer and a cross-linked polymeric gel, said electro-conductive polymer being disposed between said cross-linked polymeric gel and said ultrasonic transducer; wherein said molecules or nanoparticles are released from said electro-conductive polymer and transported to a surface of said cross-linked polymeric gel for delivery to said entity.

Advantageously, said molecules may include one or more drugs, hormones, peptides and/or other molecules for delivery to a biological tissue.

Preferably, said biological tissue include a mucosal tissue.

Advantageously, said biological tissue may include an eye or ocular adnexae, buccal or gingival mucosa and teeth, anal or vaginal mucosa, or skin.

Preferably, said surface of said cross-linked polymeric gel is shaped to match a corresponding shape of a biological tissue.

Advantageously, said entity may include an eye, and cross-linked polymeric gel may include an annular skirt for placement under an eyelid of said eye.

Preferably, said system includes an annular delivery component defining an opening, the annular delivery component including an annular housing attached to said annular skirt, the at least one ultrasonic transducer including one or more piezoelectric transducer elements disposed about an opening of said annular housing, the opening being adapted to expose a portion of an eye during delivery of said molecules and/or nanoparticles to an annular portion of said eye disposed about said portion.

Advantageously, the system may include an optically transparent membrane that contacts the exposed portion of the eye during said delivery.

Preferably, said material is also disposed within said housing.

Advantageously, said annular delivery component may be disposable.

Advantageously, said nanoparticles may incorporate one or more drugs, hormones, and/or peptides for delivery to biological tissues.

Advantageously, the disposable annular delivery component may include an electrode to detect drug level.

Advantageously, the electrode may also be adapted to deliver electrical energy to said electro-conductive polymer.

Preferably, the system includes a handle rotatably coupled to said disposable annular delivery component.

Preferably, said handle and disposable annular delivery component are mutually coupled by coupling arms extending from said handle to corresponding openings located at substantially opposing sides of said annular delivery component Preferably, the system includes a power supply for said at least one ultrasonic transducer, the power supply being disposed within said handle.

Preferably, said power supply is electrically coupled to said at least one ultrasonic transducer via electrodes of respective ones of said coupling arms.

Advantageously, the disposable annular delivery head may include an electronic circuit for simultaneous delivery of electrical energy to the one or more ultrasonic transducer elements and to the electro-conductive polymer.

Advantageously, the amount of electrophoresis and sonophoresis can be independently controlled by the DC and AC components in the applied signal.

Advantageously, said molecules may include an ink or dye for print

Figure 3:
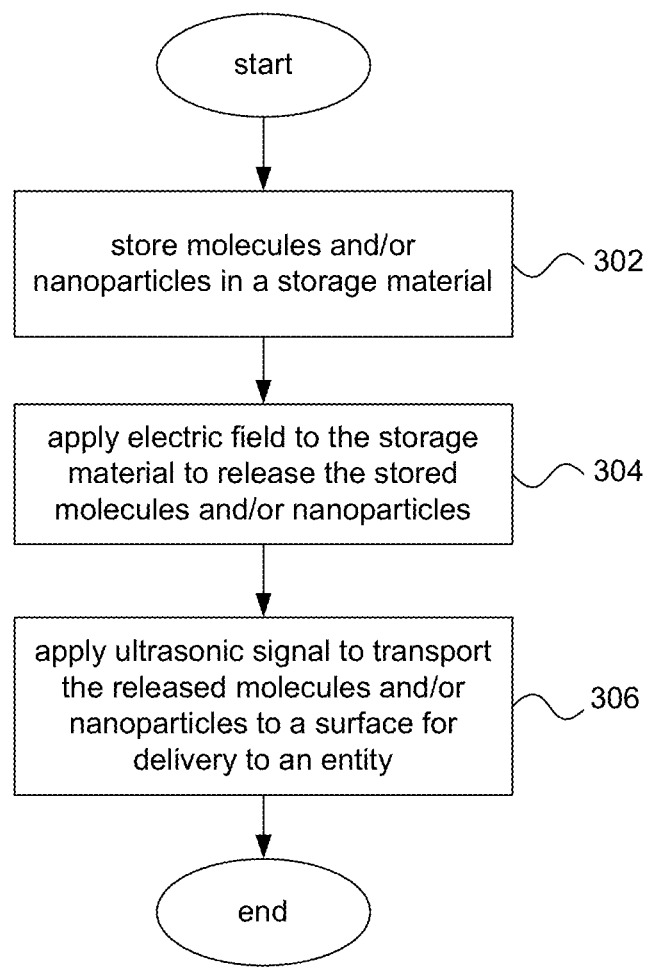

The delivery system uses a delivery process as shown in FIG. 3 to deliver molecules and/or particles stored within the storage material 102 to an exposed surface 110 of the storage material 102 for delivery to an entity 112 placed in contact with that surface 110, as described below. The molecules may be drugs, hormones, and/or peptides or other molecules suitable for delivery to biological tissue. The molecules may also be coated by lipids, in which case they are referred to as liposomes. The particles are preferably of nanoscale dimensions to enhance their transport, and accordingly are hereinafter referred to as nanoparticles. However, it should be understood that the delivery process and system can be applied to larger particles if desired, providing that such particles have sufficient mobility through the storage material 102 during use of the process, as described below, to provide a useful flux of those particles to the delivery surface 110. In particular, the delivery of nanoparticles can be used to deliver drugs, as described in Takeuchi H, Yamamoto H, Kawashima Y (2001), *Mucoadhesive nanoparticulate systems for peptide drug delivery*, Adv Drug Rev, 47:39-54. Processes for forming polymer-coated nanoparticles are also described in Cui F, Qian F, Yin C (2006), *Preparation and characterisation of mucoadhesive polymer-coated nanoparticles*, Int J Pharm. 316:154-161.

As shown in FIG. 3, the delivery process begins at step 302 by storing within the storage material 102 molecules and/or nanoparticles to be delivered. The molecules and/or nanoparticles can be introduced into the storage material 102 using a standard syringe or can be incorporated within the storage material 102 during its formation, although it will be apparent to those skilled in the art that other methods can alternatively be used. In any case, the molecules and/or nanoparticles can be stored within the storage material 102 while it is configured as shown in FIG. 1 or it may be so configured at a later time, as described below. The molecules and/or nanoparticles have a net electrical charge which causes them to be substantially bound within the storage material 102. Whether the net electric charge is positive or negative depends upon the nature and type of the particular electro-conductive polymer or polymeric gel used. For example, the most preferred electro-conductive polymer is polypyrrole, which has a positively charged polymer matrix that selectively binds negatively charged molecules and/or nanoparticles. The preferred polymeric gel is cross-linked hydroxyethyl methacrylate, which is capable of binding either positively or negatively charged molecules or nanoparticles, depending on the nature of the crosslinking agent and the polarity of the polymer gel matrix. However, in addition to binding based on the charge of the molecules of nanoparticles, polymer gels are also porous and are capable of binding by physical entrapment within their pores. If an electro-constrictive polymer is used as the storage material 102, the electric field causes a reduction in the volume of the electro-constrictive polymer, thereby further enhancing the transport of the molecules and/or nanoparticles from the electro-constrictive polymer.

Having stored the molecules and/or nanoparticles within the storage material 102, the storage material 102 can be stored for subsequent use and may be provided to another party for use with that party's delivery system. In either case, when it is desired to deliver the stored molecules and/or nanoparticles to an entity, the storage material 102 is configured as shown in FIG. 1 (if it is not already so configured). At step 304, an electric field is established within the storage material 102 by way of the voltage source 106, which typically generates DC voltages up to about +1.5 VDC. A typical distance from the applied DC voltage to the external entity 112 is about 10 mm, producing an electric field of about 150V/m. In an alternative embodiment, the electric field is pulsed by an alternating voltage (typically varying between about −0.5V and +0.6V) to produce pulsatile release of the stored molecules and/or nanoparticles. The alternating voltage is preferably in the form of a symmetrical 3-second square wave having a frequency of about 0.3 Hz. In either embodiment, the electric field releases the bound molecules and/or nanoparticles stored within the storage material 102, allowing them to diffuse and/or otherwise be transported through the storage material 102.

At step 306, an ultrasonic signal (typically of 40 kHz) is generated in the storage material 102 by way of the signal generator 108 typically providing a peak-to-peak voltage of 20 V to the ultrasonic transducer 104. This provides an acoustic flux of approximately 200 mW cm$^{-2}$. The ultrasonic signal greatly increases the mobility of the released molecules and/or nanoparticles (a phenomenon referred to as sonophoresis), effectively transporting them to the delivery surface 110 of the storage material 102, thus allowing them to be delivered to an external entity 112 contacted by the delivery surface 110 of the storage material 102. Additionally, the ultrasonic signal is transmitted through the storage material 102 to the surface of the entity 112, where it can also enhance the permeability of that surface.

Although the electric field has been described above as being applied prior to the application of the ultrasonic signal, it will be apparent to those skilled in the art that it is not necessary that the electric field precede the application of the ultrasonic signal, but may alternatively be applied or otherwise controlled at the same time as the ultrasonic signal in order to control the release and/or transport of the stored molecules and/or nanoparticles.

Figure 2:
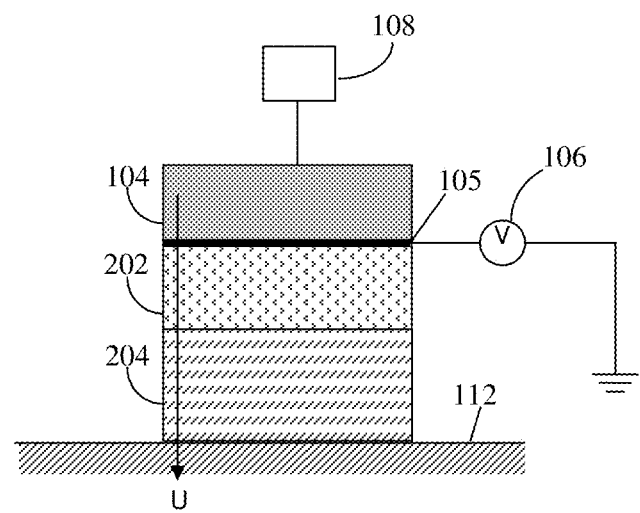

In a second preferred embodiment, as shown in FIG. 2, the storage material 202 is an electro-conductive polymer, and a cross-linked polymeric gel material 204 is applied to the surface of the storage material 202 opposite to the ultrasonic transducer 104 to provide a biocompatible surface for delivery to biological tissues. As with the first preferred embodiment described above, the polymeric gel material 204 may or may not contain water. In this second preferred embodiment, the molecules and/or nanoparticles released from the storage material 202 are transported through the polymeric gel 204 for delivery to an external entity 112 placed in contact with the otherwise exposed surface of the polymeric gel 204 opposite to the storage material 202. The electro-conductive polymer 202 and the polymeric gel 204 can be bonded together by a variety of methods, including use of an adhesive, treatment of the polymers 202, 204 with a plasma, use of a chemical reaction to cause cross linking of the polymers 202, 204 together, use of a chemical reaction to bond the polymers together without causing cross-linking, or the physical proximity and surface treatments of the polymers causing absorption of the polymers to each other. It should be understood the representation of FIG. 2 is schematic, and the polymeric gel material 204 is typically substantially thinner than shown.

The delivery process and systems can be used for a wide variety of applications, including both internal and external drug delivery, and printing, marking, or otherwise labelling animate or inanimate entities.

Figure 4:
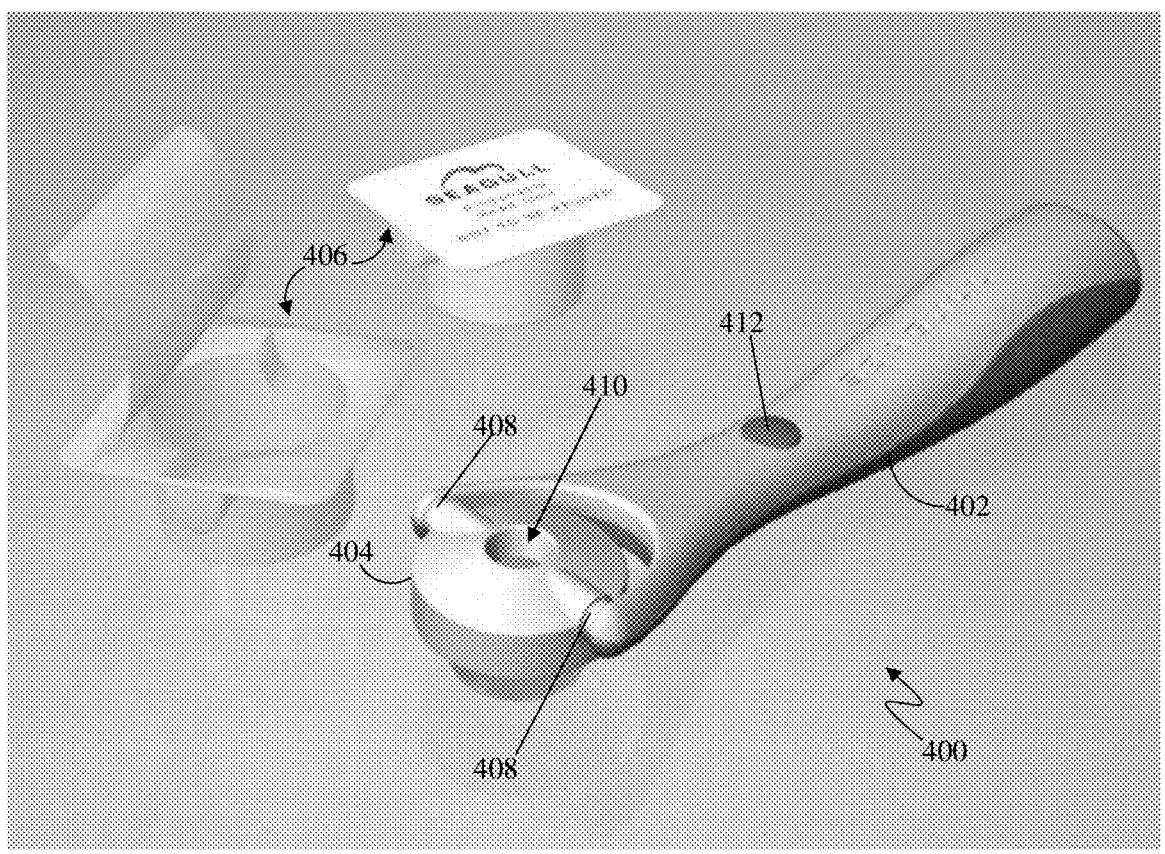

In a third preferred embodiment, as shown in FIG. 4, the delivery system is provided in the form of a handheld device 400 for the non-invasive delivery of molecules to the anterior or posterior segments of the eye. The molecules may include (i) anaesthetic compounds, (ii) antibiotic compounds, (iii) non-steroidal anti-inflammatory drugs (NSAIDs), (iv) steroid drugs, and/or (v) peptides. The delivery device 400 has two major components: a reusable handle 402, and a disposable applicator head 404. The handle 402 is provided in two forms, only one of which is capable of being sterilised in an autoclave.

Figure 5:
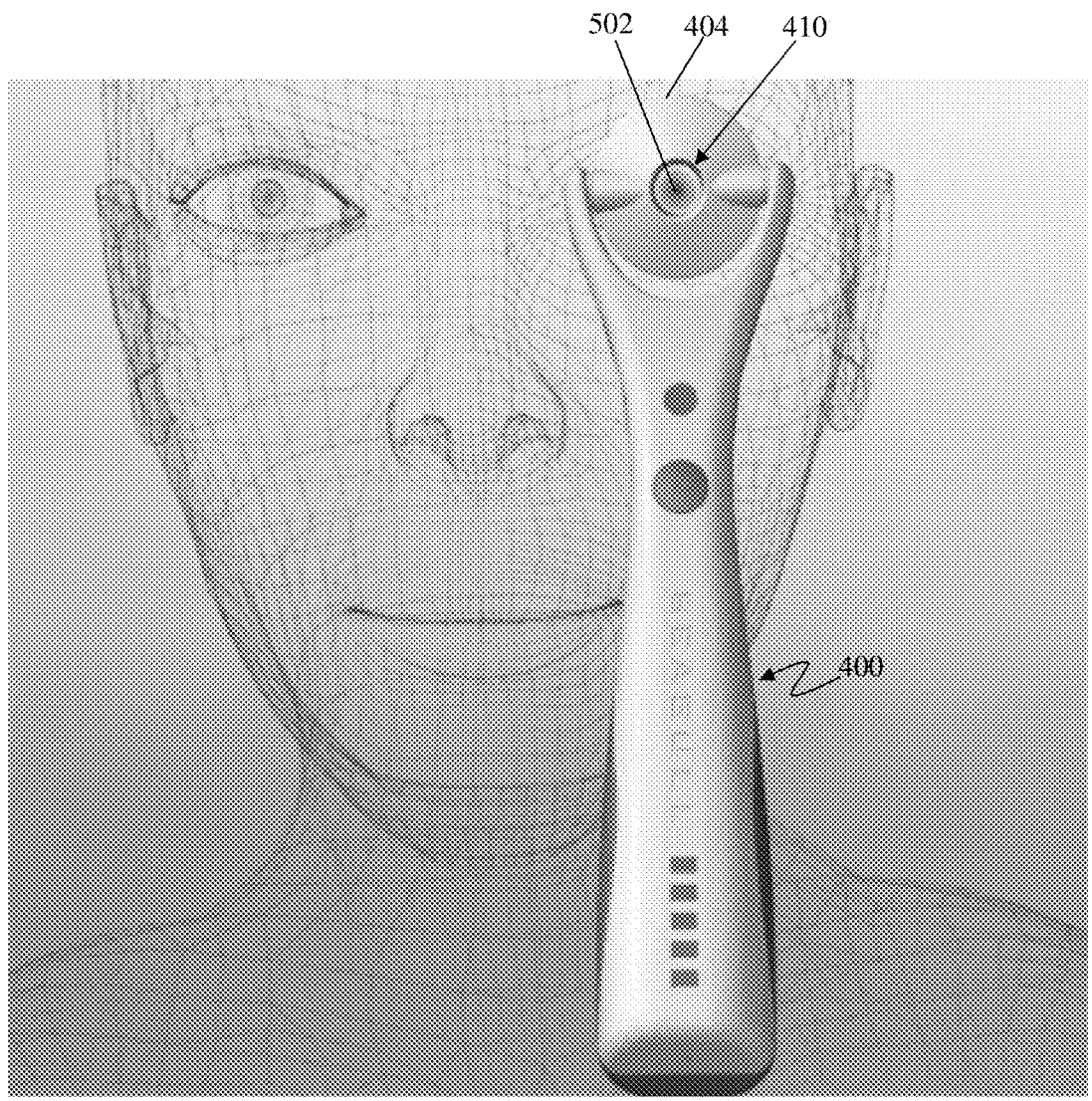

The disposable applicator head 404 is preferably provided separately in a sterile form, packaged in a bubble-package 406. The applicator head 404 is generally annular in shape and includes two opposed and radially outwardly directed cylindrical openings into which correspondingly shaped and inwardly directed projections 408 of the handle 402 are inserted to pivotally couple the applicator head 404 to the handle 402. This arrangement allows the applicator head 404 to pivot about the securing projections 408 to facilitate alignment to the eye. However, the applicator head 404 could alternatively be coupled to the handle by way of an articulated coupling that provides additional degrees of freedom for mating the applicator head 404 to the eye. The applicator head 404 contains a storage material 708 in the form of a polymer gel or an electro-conductive polymer that stores the desired molecules and/or nanoparticles for delivery to the eye, as shown in FIG. 5. If the storage material 708 is an electro-conductive polymer, the voltage generated by a voltage source located within the handle 402 induces an electrochemical electrostatic, and/or electro-constrictive-based release of the stored molecules and/or nanoparticles otherwise bound to the electro-conductive polymer 708. This release is further enhanced when return current from the eye itself forms part of the electrical circuit, thereby driving the released molecules and/or nanoparticles into the eye by ionophoresis or phonophoresis, as described in Tyle P, Agrawala P. "*Drug Delivery by Phonophoresis*", Pharmaceutical Research, 6(5):355-361, 1989) ("Tyle and Agrawala"). The ultrasonic energy transmitted from the applicator head 504 to the eye enhances the diffusion of the molecules and/or nanoparticles, through the storage material 708 for delivery to the eye. Furthermore, the ultrasound is also transmitted to the eye itself, thereby enhancing the permeability of the eye tissues during delivery, a phenomenon known as sonophoresis. The delivery of the molecules and/or nanoparticles, to the anterior and posterior segments of the eye is thus assisted by the ultrasound. The electrically induced release of the stored molecules and/or nanoparticles from the electro-conductive polymer 708 allows the rate and total amount of the released and hence delivered molecules and/or nanoparticles to be controlled by controlling the duration and magnitude of the electric voltage applied to the storage material 708. For example, in response to pressing a 412 button on the handle 402, the delivery system 400 can be configured to apply a fixed (or selected) DC or AC voltage to the storage material 708 for a fixed (or selected) period of time, corresponding to a fixed (or selected) fluence or dosage of the delivered molecules and/or nanoparticle.

As shown in FIGS. 4 to 8, the disposable applicator head 404 is generally annular in shape, defining a central hole 410 of diameter 11 mm. The applicator head itself 404 is provided in a range of external diameters from 15 mm to 20 mm to deliver molecules and/or nanoparticles to targeted sites on the eye. For example, a 15 mm diameter applicator head is used for delivery only to the cornea and limbus areas, whereas a 20 mm diameter applicator head is used to target both the cornea/limbus areas as well as the insertion of the extraocular muscles. It can be desirable to target the extraocular muscles to immobilise the eye in addition to anaesthetising the eye (cornea and limbus).

As shown in FIG. 5, the delivery device 400 is applied to the eye 502 of a patient, and can be used to deliver an anaesthetic compound into the anterior and posterior segments of the eye 502 during eye surgery. The central opening or hole 410 through the applicator head 404 allows a surgeon to accurately align and position the applicator head 404 to be centred with respect to the cornea and the eye-pupil by being able to view the cornea and eye-pupil through the central opening in the applicator head 404. Although the central opening 410 is shown as passing right through the applicator head 404, it is preferred that the opening be closed at the delivery end by a thin, optically transparent polymer membrane that contacts the eye 502 during delivery (in a manner analogous to a contact lens).

Figure 7:
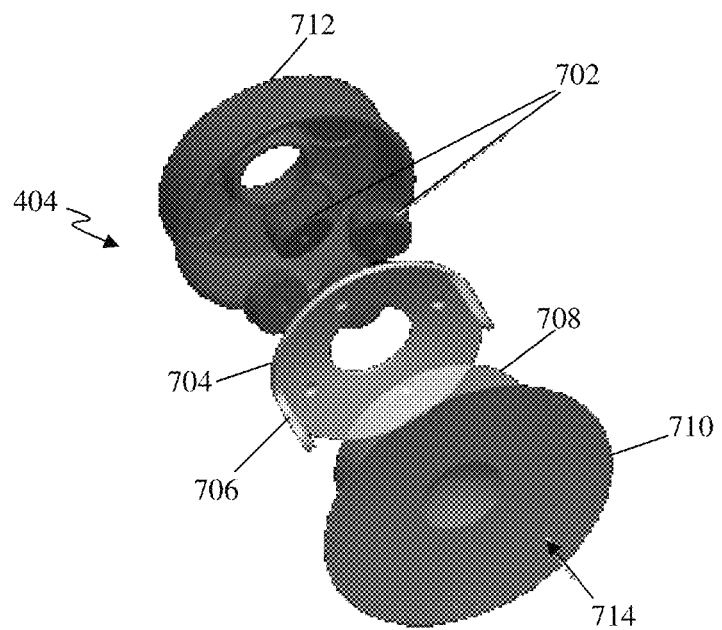
Figure 8:
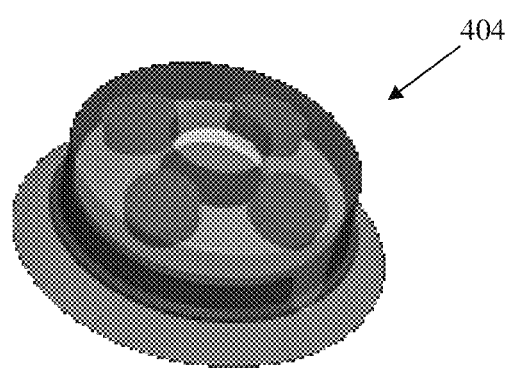
Figure 9:
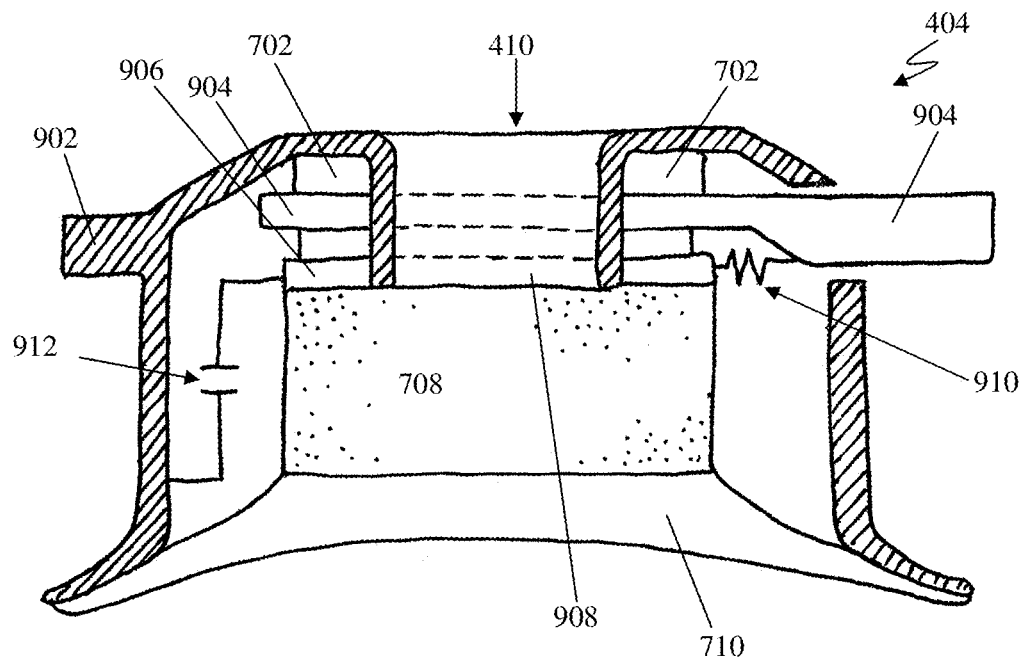
Figure 22:
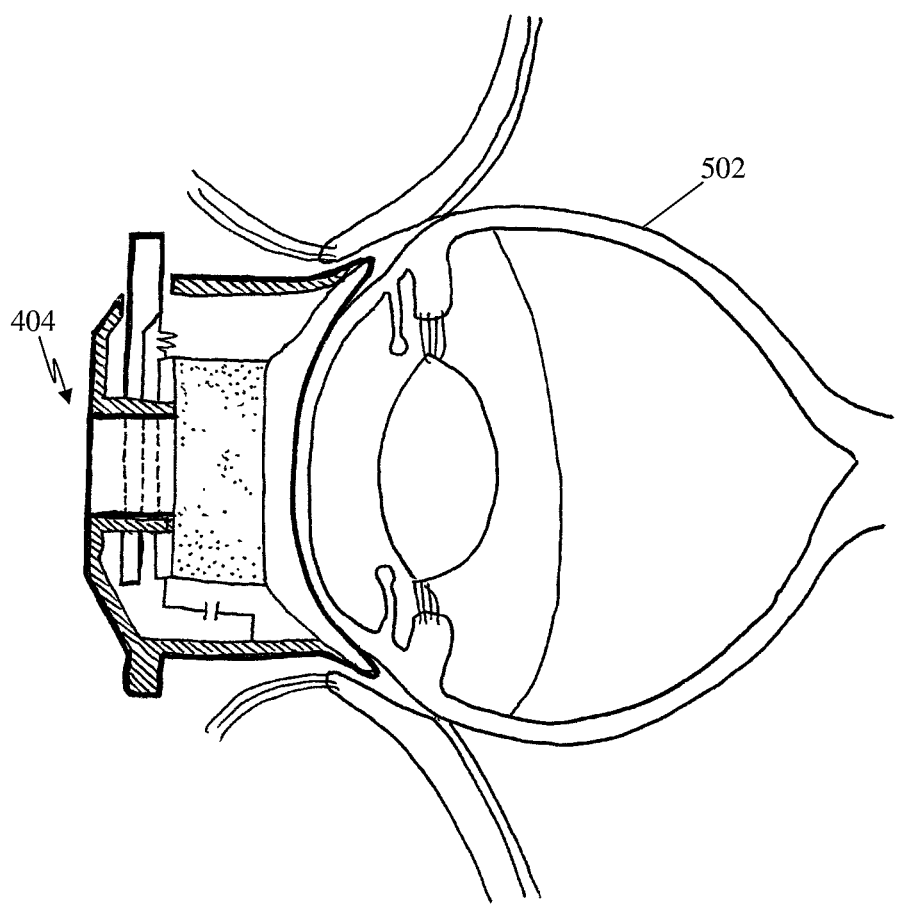

FIGS. 7 and 8 are respectively exploded and assembled views of the major components of the applicator head 404, omitting (for reasons of clarity) details such as the electrical contacts to the power supply located in the device handle 402. As shown in FIG. 7, the applicator head 404 includes a piezoelectric transducer having four piezoelectric transducer elements 702 distributed about the central hole 410. In an alternative embodiment (not shown), only a single annular-shaped piezoelectric transducer element is used. In either embodiment, the electrical contact to the piezoelectric transducer is included within an electrically conductive housing 712, as described below. A part-spherical, annular metal contact ring 704 provides the support and the electrical contact for the storage material 708 which is in contact with the surface of the contact ring 704. Thus the electrical contact for the piezoelectric transducer is separate and insulated from the electrical contact for the storage material 708, as described below. The contact ring 704 includes two metal locating arms 706 extending orthogonally from the contact ring to locate the storage material 708 therebetween. The contact ring 704 is disposed between the piezoelectric element 702 and the storage material 708, which as described above can be either a polymeric gel or an electro-conductive polymer. A moulded polymeric gel skirt 710 provides the biocompatible delivery surface in contact with the eye, and the peripheral skirt is slid underneath the patient's eyelid during use, as shown in FIG. 22. By forming the skirt from an electrically conductive material, or by forming an electrically conductive surface coating on the skirt, a return path for electrical current is provided. The bottom face or delivery surface 714 of the moulded gel skirt 710 is generally concave in shape to fit the anterior eye surface, and as described above preferably includes a thin, optically transparent membrane of the gel, located over the central opening 501.

Finally, an electrically conductive housing 712 is provided to encase the piezoelectric elements 702, the ring contact 704 and the electro-conductive polymer 708 to provide an integral applicator head 504, as shown assembled in FIG. 8. As described above, the applicator head 504 can be sold or otherwise provided separately from the remainder of the delivery device, as a disposable (or possibly rechargeable) component.

FIG. 8 is a cross-sectional side view of the annular applicator head 404, showing how the various components are electrically coupled. The electrical interface between the disposable annular applicator head and the device handle provided by two radially directed electrodes 902, 904 of opposite electrical polarities located within the cylindrical openings of the applicator head 404, as described above. A first electrode 902 of these two electrodes 902, 904 is cylindrical in shape and projects from the outer housing 712, to which it is electrically connected. A second electrode 904 of these two electrodes 902, 904 includes an outwardly directed cylindrical portion projecting from the housing 712 and a disc-shaped portion disposed between the piezoelectric transducers 702 on one side and an annular disc-shaped electrical insulator 906 on the other. These electrodes 902, 904 form electrical connections with corresponding mating electrodes at the ends of the inwardly directed projections 408 of the device handle 402.

The electrodes 902, 904 simultaneously supply electrical energy to both the piezoelectric transducers 702 and the storage material 708 as a DC-biased high-frequency AC signal. High-frequency acoustic energy is transmitted through the gel into the eye in the following manner: the electrodes 501, 502 connect directly across and deliver high-frequency AC energy to the piezoelectric transducer(s) 702, which convert this electrical energy into acoustic energy. The resulting acoustic energy is then coupled through the annular disc-shaped portion of the second electrode 904, the electrical insulator 906 and an annular disc-shaped intermediate electrode 908 into the electro-conductive/nanoparticle polymer 708 and the cross-linked gel 710 into the patient's eye. As the piezoelectric transducers 702 are electrically insulating, they do not provide any substantial electrical path for DC current.

Figure 10:
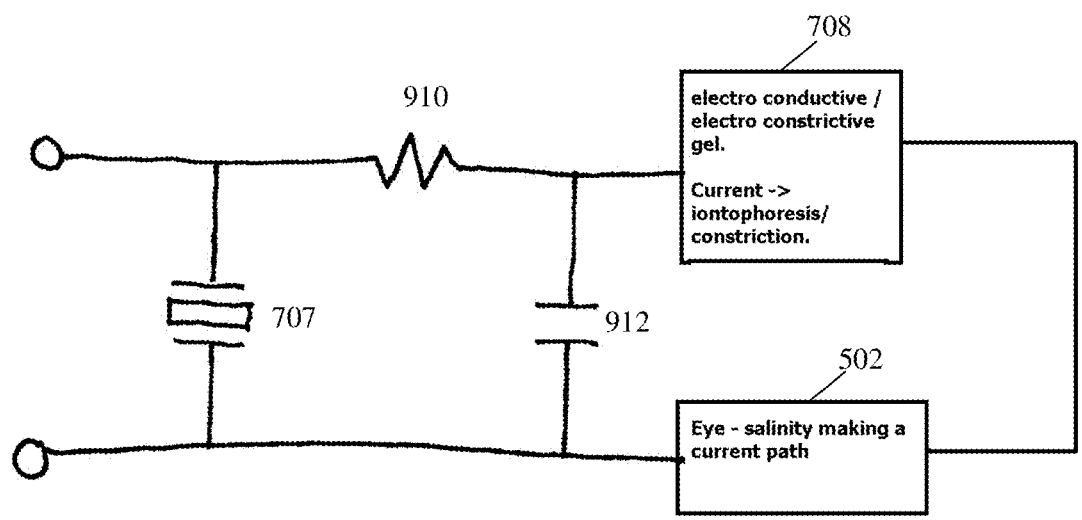

DC electrical energy is transmitted through the gel 710 into the eye in the following manner: current is conducted through the second electrode 904, through a resistor 910 into the intermediate electrode 908. Note the insulator 906 prevents an alternate current path through the transducer interface. The high frequency AC component of the applied signal is dramatically reduced by a low-pass filter formed by the resistor 910 and a capacitor 912 electrically connected between the intermediate electrode 908 and the grounded housing 712 (electrically coupled to the patient's eye 502), as will be apparent from the equivalent circuit diagram of FIG. 10. The result of this filtering effect is to substantially remove the DC or very low frequency AC component of the electrical signal applied to the second electrode 502. This DC component is then passed through the electro-conductive/electro-constrictive polymer 402 and through the cross-linked gel 404 into the patient's eye 502, transporting nanoparticles with it by iontophoresis, as described above. The patient return current path is via the housing 712, the current returning via the patient's eyelid.

In this embodiment, the AC and DC components of the electrical signal applied to the disposable annular delivery head can be independently selected or controlled by the power supply located within the handle 402 to independently control the levels of electrophoresis/iontophoresis, sonophoresis and electro-constriction (if an electroconstriction polymer is used as the storage material) in the electro-conductive gel.

Another advantage of this arrangement is the ability to determine the condition of the storage material 708 and the amount of drugs or other stored species remaining in the storage material 708, because the amount of free ions in suspension can readily be measured by the resultant current that flows when a low-frequency AC voltage is applied to the first and second electrodes 902, 904. The amount of DC across the capacitor 912 can be controlled by a DC offset or by the values of the R-C network. As the return current path is via the patient's eyelid, there is no need for additional electrodes to complete the patient circuit.

Figure 6:
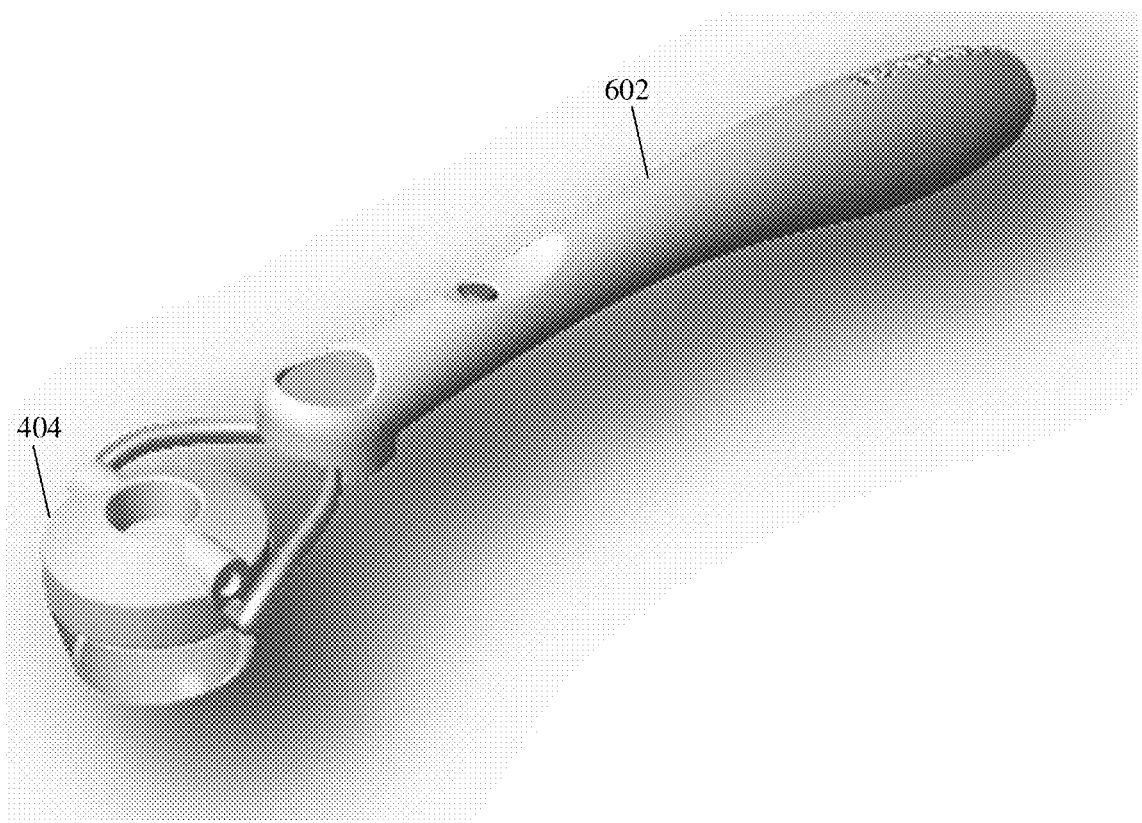

FIG. 6 shows an alternative form of handle 602 for use with the applicator heads 404, and it will be apparent that a wide variety of different handle types can be used with the applicator heads 404. For example, not only can handles be provided in different shapes and sizes for different types of users and/or applications, but also different power supplies can be provided within these different handles. For example, the simplest type of power supply might include a simple battery with an on-off button that simply connects and disconnects the battery directly to the applicator head 404. Conversely, a more complex power supply might be rechargeable and include selectable and/or programmable DC and/or AC voltages, allowing sophisticated users to select different signal magnitudes, frequencies, and waveforms suited to particular applications. For example, the power supply could be pre-configured for one or more predetermined types of applicator head with particular combinations of drugs and polymers so that the user could select what dosage of drug is to be delivered and the device could power the applicator head with a suitable signal and then generate an indication (for example, an audible signal) when the desired dosage should have been delivered or absorbed by a particular type of biological tissue.

The handheld delivery devices described above provide means for non-invasive drug delivery to the eye that overcome the risks associated with injection into the eye. It provides a painless, rapid and accurate means of delivering local anaesthetic, antibiotic, and/or anti-inflammatories to the eye for surgery. It facilitates a safe and relatively comfortable delivery of drugs targeted for the retina that would otherwise require injection into or around the eye, or delivered systemically, exposing the patient to potential unwanted side effects, Although the handheld delivery device 400 described above is particularly suited for delivery of drugs and other molecules to the eye, it will be apparent that the delivery surface 714 of the device need not be annular and can alternatively be shaped to fit the contours of other body parts or biological tissues to which it is desired to deliver drugs and/or other molecules. For example, the delivery surface 714 could be shaped to fit the teeth and/or jaw bones for delivery of molecules to the buccal or gingival mucosa and teeth, or shaped to fit the contours of the anus or vagina for delivery of molecules to the anal or vaginal mucosa, or shaped for transdermal delivery of molecules. Additionally, the delivery component or head may include an electrode to detect drug levels. That electrode may be the same electrode used to deliver electrical energy to the storage material, or may be a separate electrode.

Alternatively, the delivery systems described above can be used to deliver one or more electrically charged chemical compounds, including a dye or ink that carries an electric charge, or is contained within a particle that carries an electric charge. The dye or ink can be deposited at a desired depth below the surface of the entity to which the dye or ink is applied, which may include almost any material, and in particular may include paper, plastic, or skin. In this application, the depth of the deposit is determined by the intensity and/or duration of the ultrasonic signal, and the release of the ink or dye can be controlled by controlling the electric field applied to the storage material.

When applied to skin, the ultrasonic signal also enhances the permeability of the skin, and hence the transport of the ink or dye into the skin. For example, a temporary tattoo lasting for a relatively short period of time can be produced on the skin of an individual by using a relatively low power ultrasonic signal to deposit the ink or dye within the outer most epidermal layer of the cells in the skin. In contrast, a tattoo can be made to last for a relatively long period of time ("a permanent tattoo") by using an ultrasonic signal of relatively high power to deposit the ink or dye in the dermal layer of cells in the skin. Temporary tattoos can be useful for a variety of applications, including applications in the cosmetic industry, for example. Permanent tattoos can be used to provide an efficient and painless means for identifying domestic or experimental animals. In either case, a significant advantage of the processes described herein is that the ink or dye can be deposited within the skin without physically penetrating the skin by any part of the delivery device or system. This non-invasive process thus reduces the risk of infection and/or contamination.

Example 1

Figure 11:
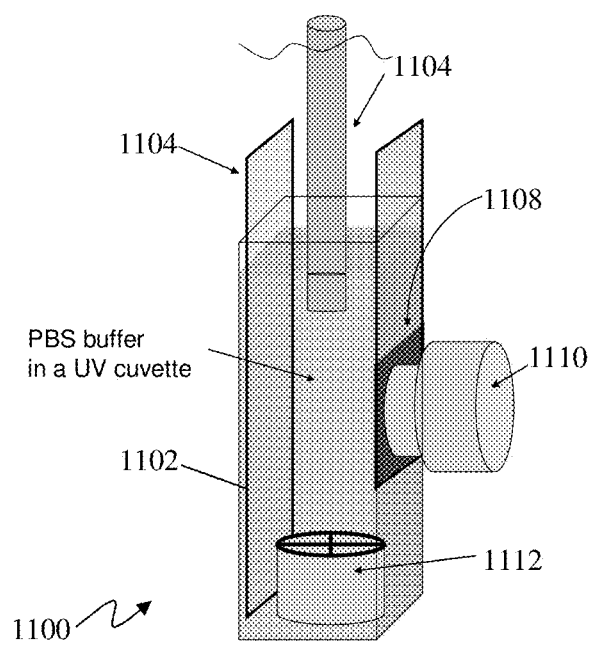

As shown in FIG. 11, an electrochemical cell 1100 was constructed by filling a plastic UV cuvette 1102 with a PBS buffer. The PBS buffer (3 ml) is a phosphate buffered saline having a pH of ~7.4 at 25° C. and contains 0.01 M phosphate buffer, 0.0027 M potassium chloride and 0.137 M sodium chloride. An Ag/AgCl (saturated NaCl) reference electrode 1104 was partially inserted into the PBS buffer. An auxiliary electrode 1106 formed from stainless steel mesh of dimensions 4×0.8 cm$^2$ was attached to one side of the cuvette, and a working electrode 1108 was attached to the opposite side of the cuvette 1102. The working electrode 1108 was prepared by forming a polypyrrole film (of dimensions 0.8×0.8 cm$^2$) on one end of gold mylar substrate was prepared from aqueous 0.2 M pyrrole containing 0.1 M sulforhodamine B dye as the supporting electrolyte. The amount of polypyrrole was controlled by applying a constant current density of 1.0 mA/cm$^2$ to the solution for 6 minutes. This as-prepared polypyrrole film was then throughout rinsed with Milli-Q water and then dried in air. A piece of stainless steel mesh was used to make the electrical contact to the gold mylar at another end. According to total consumed charge for the growth of polypyrrole, the amount of dye in the polypyrrole film was estimated at ~198 μg.

The working electrode 1108 and an ultrasound transducer 1110 were respectively attached to the inner and outer faces of one of the walls of the plastic UV cuvette 1102, as shown. The ultrasound transducer 1110 was supplied with a 15 V (peak to peak at 40 Hz) square-wave AC voltage by a function generator (not shown). A magnetic stirrer 1112 at the base of the cuvette 1102 rotated at ~90 RPM.

The cell 1100 was placed in a MultiSpec-1501 UV-VIS spectrophotometer from Shimadzu Corporation, which was used to collect UV-VIS spectra from 500 nm to 800 nm with a collection time interval of 0.1 minutes. The resulting UV-VIS spectra were used to determine the amount of dye released from the polypyrrole film.

Figure 12:
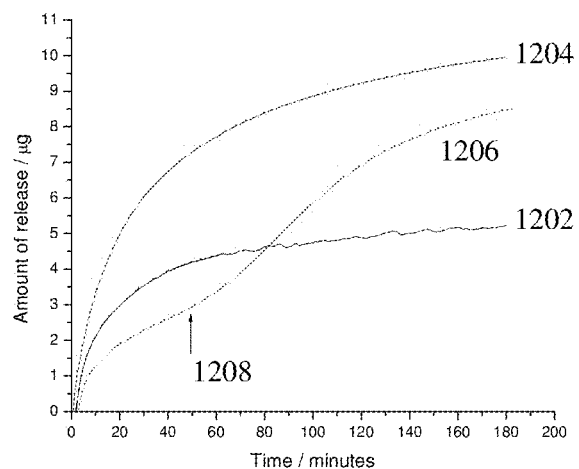

FIG. 12 is a graph showing the amount of sulforhodamine B dye in μg as a function of time in minutes under various conditions. The line 1202 shows the release of dye from polypyrrole with no electrical or ultrasonic stimulation; i.e., by natural diffusion. In contrast, the top line 1204 represents the release of dye with ultrasound stimulation, which clearly increases the rate of release by about a factor of two. In the initial linear regime over the first few minutes, the rate of release under natural diffusion was about 0.2 μg/min, and with ultrasound was 0.33 μg/min After 180 minutes, the total amount of dye released was 5.2 μg and 9.9 μg. The effect of ultrasound was confirmed by an intermediate line 1206 in which the dye was initially released under natural diffusion, and at approximately 50 minutes the ultrasound transducer 1110 was powered, which dramatically increased the rate of release, as shown by the arrow 1208 in FIG. 12. However, in all cases the final amount of release dye in each case was less than 5% of the total amount of dye in the polymer film.

Figure 13:
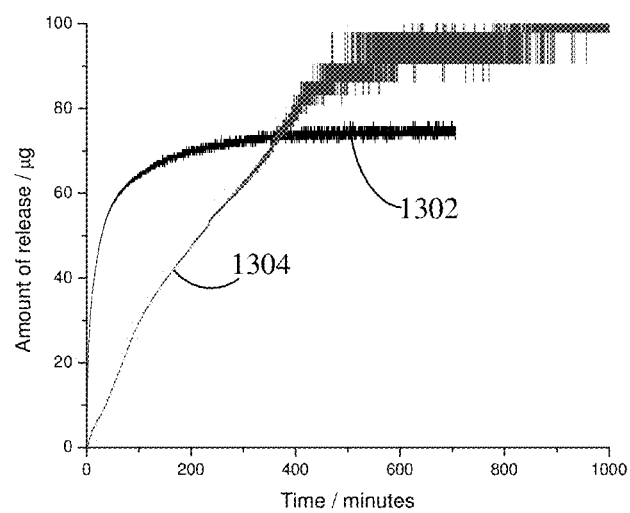

The effect of a pulsed electric field on the release of dye was demonstrated by applying a symmetrical, three second period square-wave AC signal ranging between −500 mV and +600 mV (vs. Ag/AgCl). The lower data set 1302 in FIG. 13 shows the rate of release of the dye during the electrical stimulation as described above. In comparison with FIG. 12, it is clear that the electrical stimulation greatly enhances the release of dye from polypyrrole, with the rate of release in the first five minutes being ~4.4 μg/min. As shown by the second data set 1304 the rate of release is also greatly affected when the electrical stimulation is combined with the ultrasound stimulation. Although the initial rate of release indicated by the electrical stimulation alone (data set 1302) is greater than when both stimuli are applied, it will be apparent that this rate of release quickly decreases with time, whereas under combined electrical and ultrasound stimulation (data set 1304), the rate of release remains approximately linear over at least the first 400 minutes, with the rate of release over 8 hours being 0.19 μg/min, and the final amount of dye released from the polymer being about 100 μg, being approximately 50% of the total amount of dye in the polymer.

Considering that the polypyrrole is a poly cationic matrix doped with anionic dye molecules, ion exchange would occur between the dye and the anions in the PBS. Since the dye is relatively big (Mw: 580.7), most of the dye molecules might be physically entrapped in the polymer matrix, so that only a small fraction of them were released (~2.5%). Ultrasound may increase the rate of release by opening up the pores.

The data shown in FIG. 13 demonstrates that electrical stimulation significantly enhances the rate and amount of release. At a reduction potential, the positive charge along the polypyrrole chain was neutralised, and the anionic dye was released from the polymer matrix. At an oxidation potential, the polypyrrole became positively charged and incorporated anions from the supporting electrolyte. Repetitive potential pulsing promoted anionic exchange and enhanced the rate of release in a short time period.

Example 2

Figure 14:
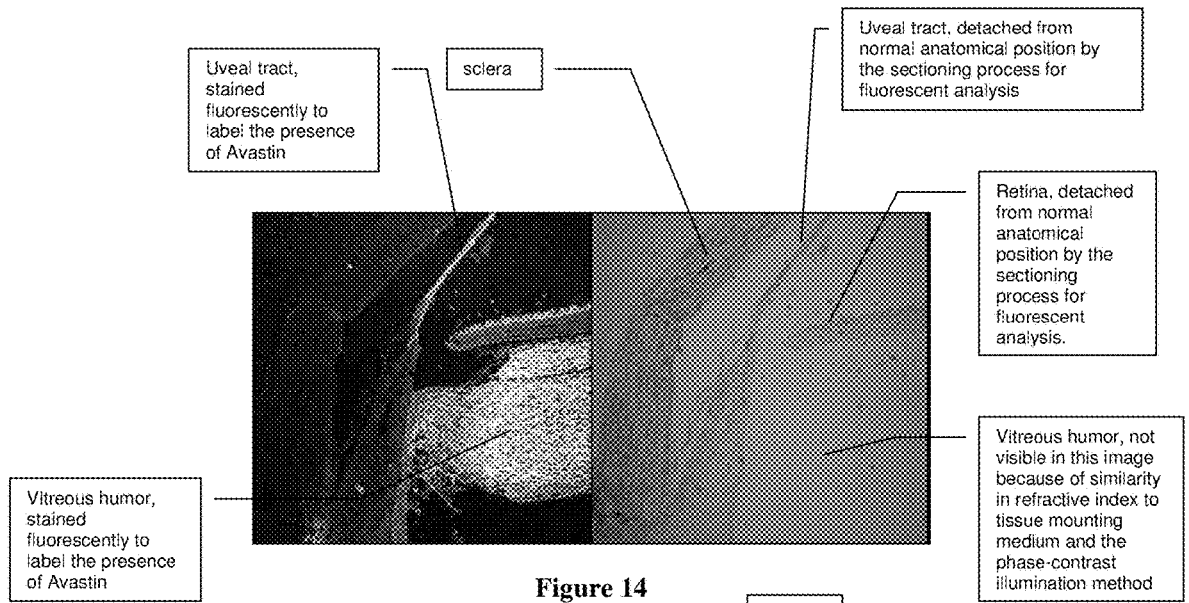
Figure 15:
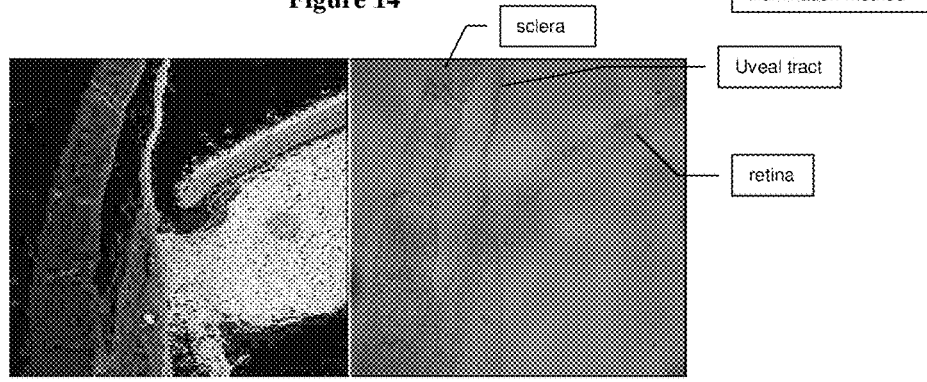
Figure 16:
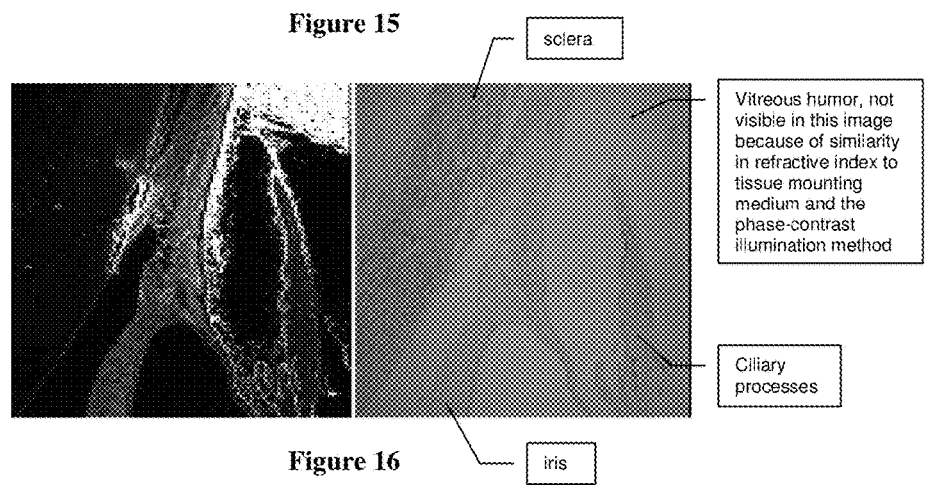
Figure 17:
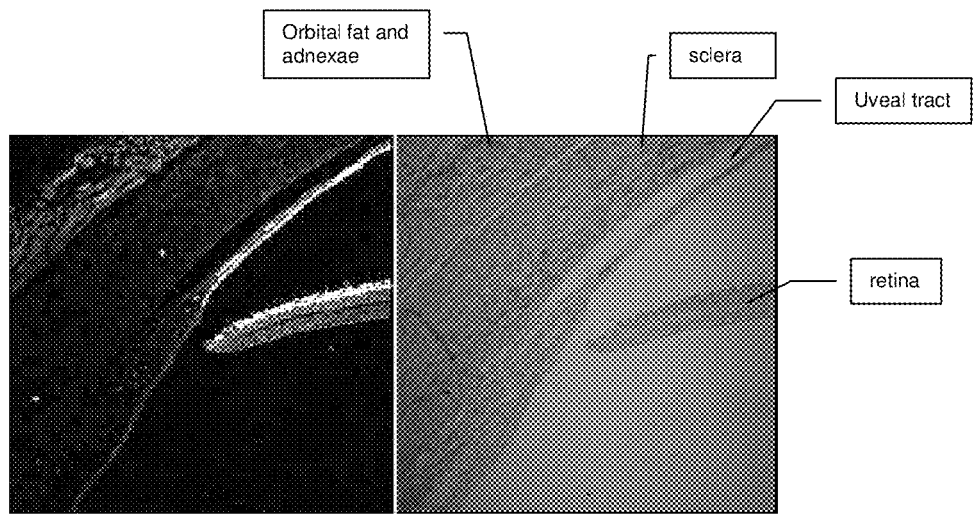
Figure 18:
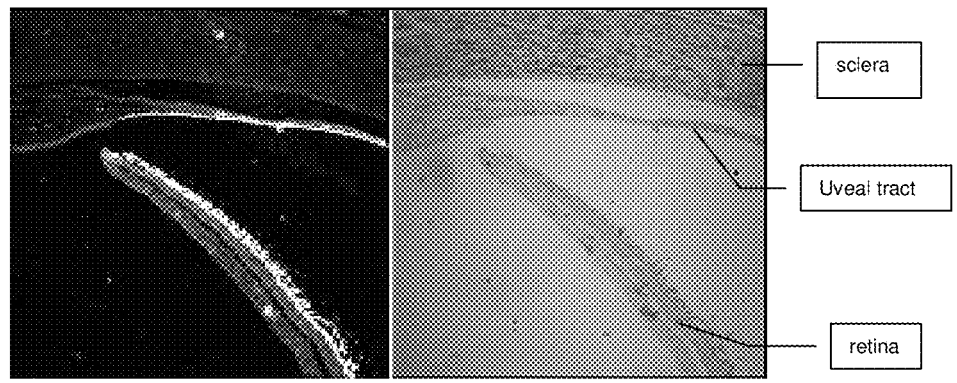
Figure 19:
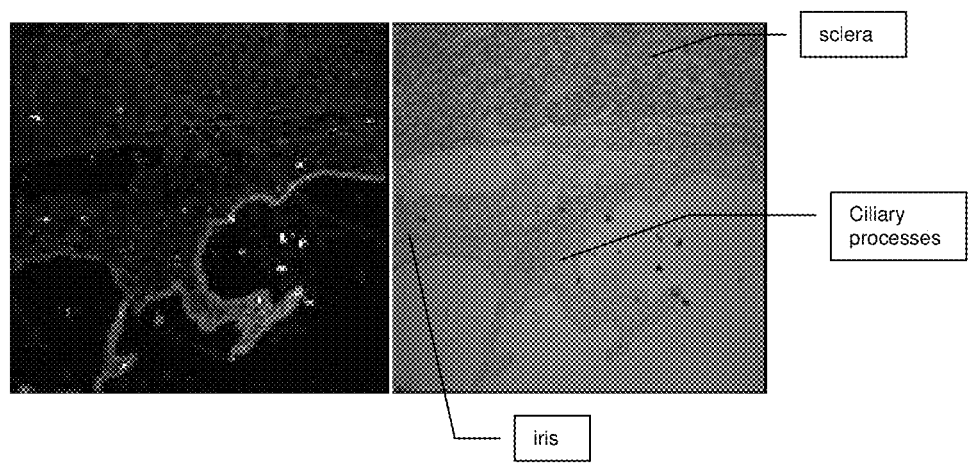

As described above, the delivery system or device can be used to deliver molecules and/or nanoparticles to the eye of a patient. Once delivered to the surface of the eye, the molecules and/or nanoparticles can penetrate the outer surface of the eye and diffuse to the posterior parts of the eye. For example, FIGS. 14 to 19 are optical microscope images of sectioned rabbit eyes imaged by Differential Interference Contrast (DIC) phase contrast imaging and fluorescence imaging, illustrating the distribution of the monoclonal antibody Avastin to various parts of the eye. Each of these six Figures includes two panels, comprising a left-hand panel showing a fluorescence image, and a right-hand panel showing a white light DIC phase contrast image. FIGS. 14 to 16 illustrate the distribution of Avastin delivered by intravitreal injection, whereas FIGS. 17 to 19 show the distribution of Avastin delivered from a hydrogel by sonophoresis of five minute duration. The red colour in the fluorescence images indicates a secondary antibody bound to Avastin. Consequently, the red colour indicates the location of Avastin in the tissues of the eye.

The sectioning procedure has caused the retina/choroid to separate from the sclera. In the eye (RE) with the intravitreal injection, the vitreous is visible with abundant presence (red staining) of Avastin. The vitreous humor was not visibly stained in the eye (LE) with the Sonoactuator, which indicated that no Avastin diffused out of the retina.

The ciliary body and iris are also heavily stained in the eye following intravitreal injection. That is not surprising given the role of the vitreous in providing a source for diffusion of Avastin. However, the ciliary body does not stain well in the eye following delivery from the gel with ultrasound. The passage of Avastin through the outermost layers of cells at the surface of the eye is believed to occur by the ultrasound energy acting to increase the permeability of the layers of cells in the cornea and sclera, especially in the area of the external limbus, by reversibly altering the lipid structure of the cells of the cornea and sclera. After permeating the cornea and sclera the Avastin reached the retina by diffusion in the uveal tract or in the potential space between the vitreous humor and the inner limiting membrane of the retina. The precise mechanism in the eye is not known but, Tyle and Agarwala describe related theories of the effect of ultrasound on drug permeation in the skin as being due either to cavitation effects or effects on the lipid structure of the stratum corneum of the skin.

The vitreous humor is not visible in the "white-light" DIC images because the sections are mounted on the slides using a 90% glycerol solution in order to stabilise the cover slip and the section during the confocal microscopy. The glycerol has a similar refractive index to the vitreous humor. The DIC procedure relies on phase-contrast optics, and hence structures are only visible when there are differences in refractive index.

FIGS. 17 to 19 clearly demonstrate that the Avastin has been non-invasively delivered to the choroid and retina.

Example 3

Figure 20:
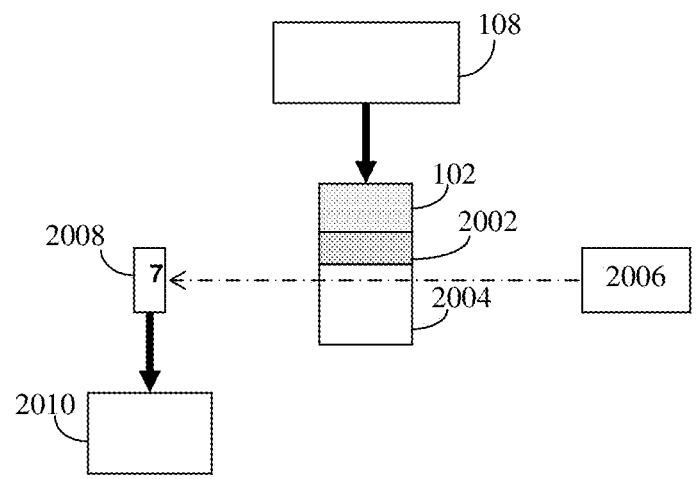

As described above, the delivery system can also be used to deliver nanoparticles to an entity. FIG. 20 illustrates an experimental arrangement for demonstrating the delivery of gold nanoparticles into an optically transparent gel 2004 under ultrasonic stimulation. The storage medium 2002 was formed by adding the gold nanoparticles to an agarose solution heated to about 70-90° C. The agarose solution was then allowed to solidify by cooling in a 4° C. environment. The result was a solid cylindrical gel 13 mm in diameter and 10 mm high containing a suspended dispersion of gold nanoparticles. This storage material 2002 was then sandwiched between the transparent gel 2004 and an ultrasonic transducer 102 driven by 20 v p-p signal @40 kHz provided by a signal generator 108, resulting in an acoustic stimulation of about 200 mWcm$^{-2}$. The beam generated by a HeNe laser 2006 is directed through the transparent gel 2004 to be received by a photodetector 2008 in order to measure the optical transmission of the laser beam through the transparent gel 2004, and thereby infer the transport of the gold nanoparticles into the transparent gel 2004. A standard computer system 2010 having an analog to digital converter (ADC) card processed the analog signal generated by the photodetector 2008 for subsequent analysis and display to a user.

In this particular arrangement, the storage material 2002 and the transparent gel 2004 were both polymeric gels formed by dissolving 0.5% agarose (w/v) in MilliQ water. Gold nanoparticles of 15 to 20 nanometre diameter were added to the heated (70-90° C.) solution of agarose in MilliQ water and the gold nanoparticles incorporated into the storage material 2002 during the setting of the agarose to form the polymeric gel.

Figure 21:
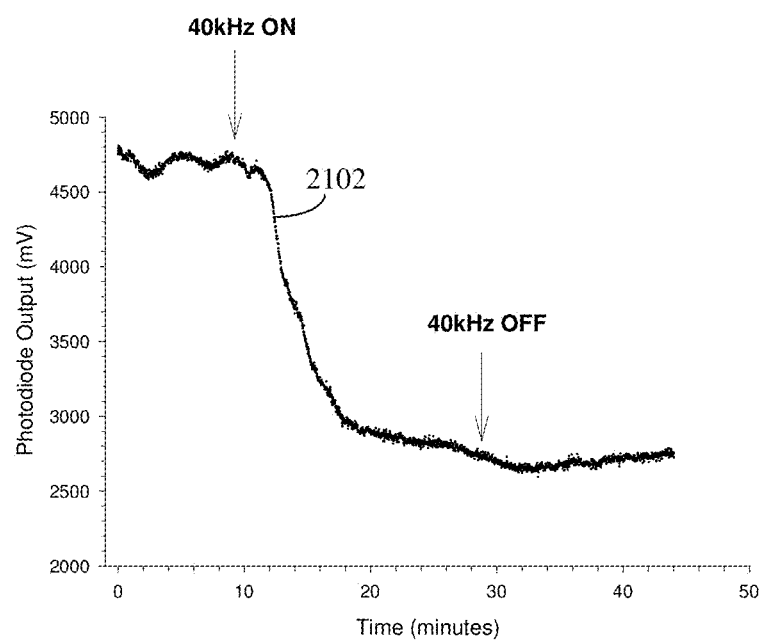

FIG. 21 is a graph of the photodiode output 2102 as a function of time. Initially, the optical transmission of the transparent gel 2004 was constant. At a time of around 8 minutes from the start of the experiment, a 40 kHz ultrasonic signal was generated by the ultrasonic transducer 102 as indicated and transmitted into the storage material 2002. In this particular arrangement, the laser beam was positioned at a point 1 mm below the interface between the clear gel 2004 and the storage material 2002. After a delay of approximately 2 minutes, the transmission of the laser beam dropped rapidly over a period of about 8 minutes, and then began to saturate at a fixed level. At a time of around 29 minutes, the ultrasonic signal was switched off, as indicated. This data clearly demonstrates that the 40 kHz ultrasonic signal was very effective in transporting the gold nanoparticles into the clear gel 2004. Scanning electron microscopy of the clear gel 2004 revealed the presence of the gold nanoparticles, confirming that they had been transported from the storage material 2002. A control experiment was performed using an identical storage material without gold nanoparticles showed a constant optical transmission that was not affected by the presence or absence of the ultrasonic signal.

Many modifications will be apparent to those skilled in the art without departing from the scope of the present invention as hereinbefore described with reference to the accompanying drawings.

What is claimed is:

1. A delivery process to non-invasively deliver molecules and/or particles to a choroid and/or retina in a posterior segment of an eye, the delivery process, comprising applying an ultrasonic signal to a polymeric material in contact with an external surface overlying sclera of the eye to:

release the molecules and/or particles substantially bound within the polymeric material, wherein the molecules and/or particles are substantially bound through:

i) the polymeric material comprising an electrical charge and the molecules and/or particles comprising an electrical charge opposite to the electrical charge of the polymeric material; and/or ii) the molecules and/or particles being physically trapped within the polymeric material;

transport the released molecules and/or particles through the polymeric material to a surface of the polymeric material that is in contact with the external surface overlying sclera of the eye; and enhance permeability of the sclera of the eye to facilitate delivery of the molecules and/or particles into a uveal tract of the eye and thereby deliver the molecules and/or particles to the choroid and/or retina in the posterior segment of the eye.

2. A process according to claim 1, wherein the molecules and/or particles substantially bound through being physically trapped within pores of the polymeric material.

3. A process according to claim 1, wherein the polymeric material is a gel.

4. A process according to claim 1, wherein the polymeric material comprises agarose.

5. A process as claimed in claim 1, wherein the polymeric material comprises an electro-constrictive polymer.

6. A process according to claim 1, wherein the polymeric material comprises a cross-linked polymer.

7. A process according to claim 1, wherein the polymeric material comprises an electro-conductive polymer.

8. A process according to claim 1, wherein the polymeric material is a hydrogel.

9. A process according to claim 1, comprising controlling the ultrasonic signal intensity and/or duration to determine a depth of delivery of the molecules and/or particles in the eye.

10. A process according to claim 1, wherein the molecules are molecules of an active agent for delivery to the choroid and/or retina, and/or the particles contain an active agent for delivery to the choroid and/or retina.

11. A process according to claim 10, wherein the active agent comprises one or more drugs, hormones, antibodies, liposomes, and/or peptides.

12. A system or device having components for executing the steps of the process according to claim 1.

13. A delivery process according to claim 1, wherein the delivery process does not comprise application of the ultrasonic signal directly to the external surface overlying the sclera of the eye.

14. A delivery process according to claim 1, wherein the molecules and/or particles are physically trapped within the polymeric material and have a net neutral charge.

15. A delivery process according to claim 1, wherein the molecules and/or particles are of equivalent size to an antibody.

16. A delivery process according to claim 1, wherein the molecules and/or particles are of equivalent size to an antibody.

17. A delivery system to non-invasively deliver molecules and/or particles to a choroid and/or retina in a posterior segment of an eye, the delivery system, comprising:
a polymeric material for storing the molecules and/or particles, wherein the molecules and/or particles are substantially bound within the polymeric material and the molecules and/or particles are substantially bound through:
i) the polymeric material comprising an electrical charge and the molecules and/or particles comprising an electrical charge opposite to the electrical charge of the polymeric material; and/or
ii) the molecules and/or particles being physically trapped within the polymeric material; and
an ultrasound generator configured to apply an ultrasonic signal to the polymeric material to release the molecules and/or particles and to transport the released molecules and/or particles through the polymeric material to a surface of the polymeric material that is in contact with an external surface overlying sclera of the eye; and to enhance permeability of the sclera of the eye to facilitate delivery of the molecules and/or particles into a uveal tract of the eye, and thereby deliver the molecules and/or particles to the choroid and/or retina in the posterior segment of the eye.

18. A system according to claim 17, wherein the particles and/or molecules are substantially bound through the molecules and/or particles being physically trapped within pores of the polymeric material.

19. A system according to claim 17, wherein the polymeric material is a gel.

20. A system according to claim 17, wherein the polymeric material comprises agarose.

21. A system according to claim 17, wherein the polymeric material comprises a cross-linked polymer.

22. A system according to claim 17, wherein the polymeric material comprises an electro-conductive polymer.

23. A system according to claim 17, wherein the polymeric material comprises an electro-constrictive polymer.

24. A system according to claim 17, wherein the polymeric material is a hydrogel.

25. A system according to claim 17, comprising a controller configured to control the ultrasonic signal intensity and/or duration to determine a depth of delivery of the molecules and/or particles in the eye.

26. A system according to claim 17, wherein the molecules are molecules of an active agent for delivery to the choroid and/or retina and/or the particles contain an active agent for delivery to the choroid and/or retina.

27. A system according to claim 26, wherein the active agent comprises one or more drugs, hormones, antibodies, liposomes, and/or peptides.

28. A system according to claim 17, wherein the ultrasound generator configured to apply an ultrasonic signal comprises at least one ultrasonic transducer coupled to the polymeric material.

29. A system according to claim 17, wherein the system is a hand-held device.

30. A system according to claim 17, wherein the system comprises a removable delivery component incorporating the polymeric material.

31. A system according to claim 30, wherein the delivery component also comprises one or more ultrasonic transducers.

32. A system according to claim 30, wherein the delivery component is a single-use disposable component of the system.

33. A delivery system according to claim 17, wherein the delivery system does not comprise application of the ultrasonic signal directly to the external surface overlying the sclera of the eye.

34. A delivery system according to claim 17, wherein the molecules and/or particles are physically trapped within the polymeric material and have a net neutral charge.

35. A system according to claim 17, wherein the molecules and/or particles comprise antibodies.

36. A delivery system according to claim 17, wherein the molecules and/or particles comprise antibodies.

* * * * *